United States Patent [19]

Harrison et al.

[11] Patent Number: 6,071,909
[45] Date of Patent: Jun. 6, 2000

[54] PHENYLBENZIMIDAZOLE DERIVATIVES AS LIGANDS FOR GABA RECEPTORS

[75] Inventors: Timothy Harrison, Great Dunmow; Timothy Jason Sparey, Sawbridgeworth; Martin Richard Teall, Stanstead Mountfitchet, all of United Kingdom

[73] Assignee: Merck Sharpe & Dohme Ltd., Hoddesdon, United Kingdom

[21] Appl. No.: 09/341,940

[22] PCT Filed: Feb. 2, 1998

[86] PCT No.: PCT/GB98/00322

§ 371 Date: Jul. 20, 1999

§ 102(e) Date: Jul. 20, 1999

[87] PCT Pub. No.: WO98/34923

PCT Pub. Date: Aug. 13, 1998

[30] Foreign Application Priority Data

Feb. 7, 1997 [GB] United Kingdom .................. 9702524

[51] Int. Cl.$^7$ ..................... C07D 235/06; C07D 401/10; C07D 403/10; A61K 31/445; A61K 31/415
[52] U.S. Cl. ..................... 514/234.5; 544/116; 544/119; 544/370; 544/139; 544/58.4; 544/62; 546/199; 548/304.4; 514/394; 514/322; 514/255; 514/228.2
[58] Field of Search ......................... 548/304.4; 546/199; 544/370, 139, 58.4, 62, 116, 119; 514/394, 322, 255, 234.5, 228.2

[56] References Cited

U.S. PATENT DOCUMENTS

| | | | |
|---|---|---|---|
| 5,360,809 | 11/1994 | Axelsson et al. | 514/338 |
| 5,466,706 | 11/1995 | George et al. | 514/394 |
| 5,554,630 | 9/1996 | Teuber et al. | 514/338 |
| 5,554,632 | 9/1996 | Teuber et al. | 514/338 |

FOREIGN PATENT DOCUMENTS

| | | |
|---|---|---|
| 2092211 | 9/1993 | Canada . |
| 0563001 | 3/1993 | Denmark . |
| 2043471 | 2/1971 | France . |
| WO 96/33191 | 10/1996 | WIPO . |
| WO 96/33194 | 10/1996 | WIPO . |

OTHER PUBLICATIONS

Rose, Chapter 2 in Goodman and Gil's The Tharmacological Basis of Therapeutics, 8th Ed., Pergamon Press, p. 33–35, 1990.
Nagarajan et al. Condesed heterotricycles: Novel Transformation fo Dibenz[b,e][1,4]diazepinones to benzimdidazole derivatives under Vilsmeier–Haack reaction conditions, India J. of Chem., 14, 1–3, Jan. 1976.

CAS Printout for CA 2092211, Sep. 1993.
CAS Printout for EP 563001, Sep. 1993.
K.A. Wafford, et al., Mol. Pharmacol., 50: 670–678 (1996).
G.R. Dawson, et al., Psychopharmacology 121: 109–117 (1995).
Bayley, et al., J. Psychopharmacology 10: 206–213 (1996).
L.J. Bristow, et al., J. Pharmacol. Exp. Ther. 279: 492–501 (1996).

Primary Examiner—Mukund J. Shah
Assistant Examiner—Hong Liu
Attorney, Agent, or Firm—Shu Muk Lee; David L. Rose

[57] ABSTRACT

The present patent application discloses compounds having formula (I)

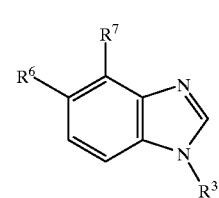

(I)

or a pharmaceutically acceptable salt thereof or an oxide thereof, wherein $R^3$ is (II),

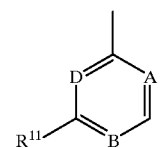

(II)

wherein A, B and D each is CH, or one or two of A, B and D is N and the others are CH; $R_{11}$ is phenyl, benzimidazolyl, or monocyclic heteroaryl all of which may be substituted one or more times with substituents selected from alkyl, alkoxy, phenyl, halogen, $CF_3$, amino, nitro, cyano, acyl, acylamino, phenyl and monocyclic heteroaryl; and one of $R^6$ and $R^7$ is hydrogen and the other is furanyl or isoxazolyl each of which may be substituted one or more times with substituents selected from halogen, alkyl, alkoxy and phenyl. The compounds are useful for the treatment of various central nervous system disorders such as epilepsy and other convulsive disorders, anxiety, sleep disorders and memory disorders.

7 Claims, No Drawings

PHENYLBENZIMIDAZOLE DERIVATIVES AS LIGANDS FOR GABA RECEPTORS

This is an application under 35 U.S.C. §371 of PCT/GB98/00322 filed on Feb. 2, 1998.

The present invention relates to a class of substituted benzimidazole derivatives and to their use in therapy. More particularly, this invention is concerned with substituted 1-phenylbenzimidazole derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta \gamma 2/3$, $\alpha 2\beta \gamma 1$, $\alpha 4\beta \delta$, $\alpha 5\beta 3\gamma 2/3$, $\alpha 6\beta \gamma 2$ and $\alpha 6\beta \delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta \gamma 2$ and $\alpha 3\beta \gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta \gamma 2$, $\alpha 2\beta \gamma 2$ or $\alpha 3\beta \gamma 2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting, and muscle spasm or spasticity, e.g. in paraplegic patients. Selective ligands for $GABA_A$ receptors may also be effective as pre-medication prior to anaesthesia or minor procedures such as endoscopy, including gastric endoscopy.

EP-A-0616807 describes a class of benzimidazole derivatives substituted at the 1-position by inter alia a phenyl moiety which in turn is substituted at the meta position by an optionally substituted phenyl, benzimidazolyl or 5- or 6-membered monocyclic heteroaromatic group, or by an alkoxy or acyl group. These compounds are stated to possess potent benzodiazepine receptor affinity, and thus to be useful in the treatment of convulsions, anxiety, sleep disorders, memory disorders and other disorders sensitive to benzodiazepine receptor binding activity. There is, however, no disclosure nor any suggestion in EP-A-0616807 that the precisely defined range of substituents prescribed for the meta position of the phenyl moiety might be replaced by any other substituent.

The present invention provides a class of benzimidazole derivatives which possess desirable binding properties at various $GABA_A$ receptor subtypes. The compounds in accordance with the present invention have good affinity as ligands for the α2 and/or α3 subunit of the human $GABA_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are $GABA_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

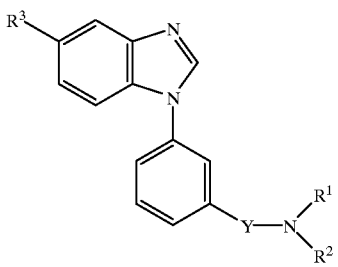

wherein

Y represents a methylene ($CH_2$), carbonyl (C=O) or thiocarbonyl (C=S) linkage;

$R^1$ and $R^2$ independently represent hydrogen, hydrocarbon or a heterocyclic group; or $R^1$ and $R^2$, together with the intervening nitrogen atom, represent an optionally substituted heterocyclic ring selected from azetidinyl, pyrrolidinyl, piperidinyl, piperazinyl, morpholinyl, thiomorpholinyl and imidazolyl;

$R^3$ represents hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$ or —$CR^a$=$NOR^b$; and $R^a$ and $R^b$ independently represent hydrogen, hydrocarbon or a heterocyclic group.

The present invention also provides a compound of formula I as defined above, or a salt or prodrug thereof, wherein $R^1$ and $R^2$ independently represent hydrogen, hydrocarbon or a heterocyclic group; or $R^1$ and $R^2$, together with the intervening nitrogen atom, represent an optionally substituted heterocyclic ring selected from azetidinyl, pyrrolidinyl, piperidinyl, piperazinyl, morpholinyl and thiomorpholinyl; and Y and $R^3$ are as defined above.

Where $R^1$ and $R^2$, together with the intervening nitrogen atom, represent an optionally substituted heterocyclic ring, this ring may be substituted by one or more, preferably one or two, substituents. Examples of optional substituents on the heterocyclic ring include $C_{1-6}$ alkyl and hydroxy. Typical substituents include methyl and hydroxy.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitable values for the substituents $R^1$ and $R^2$ include hydrogen, $C_{1-6}$ alkyl, aryl($C_{1-6}$)alkyl and heteroaryl($C_{1-6}$) alkyl, any of which groups may be optionally substituted. Typical substituents include $C_{1-6}$ alkyl, $C_{1-6}$ alkoxy and halogen.

Particular values of $R^1$ and $R^2$ include hydrogen, methyl, ethyl and pyridinylmethyl.

Suitably, one of $R^1$ and $R^2$ is other than hydrogen.

Where $R^1$ and $R^2$, together with the intervening nitrogen atom, represent an optionally substituted heterocyclic ring, this ring is suitably a piperidinyl, morpholinyl, thiomorpholinyl or imidazolyl ring, any of which rings may be unsubstituted or substituted by one or more, preferably one or two, substituents, typically hydroxy. In this context, typical values for the —NR$^1$R$^2$ moiety include hydroxypiperidinyl, morpholinyl, thiomorpholinyl and imidazolyl, preferably morpholinyl.

Suitable values for the substituent $R^3$ include hydrogen, halogen, cyano, nitro, trifluoromethyl, pyrrolyl, furyl, isoxazolyl, amino, $C_{1-6}$ alkylamino, di($C_{1-6}$)alkylamino, $C_{1-6}$ alkyl, $C_{1-6}$ alkoxy, aryl($C_{1-6}$)alkoxy, $C_{2-6}$ alkylcarbonyl, $C_{1-6}$ alkylsulphonyl and —CR$^4$=NOR$^5$, in which R$^4$ and R$^5$ independently represent hydrogen, methyl or ethyl. A particular value of $R^3$ is $C_{1-6}$ alkyl, especially methyl.

A particular sub-class of compounds according to the invention is represented by the compounds of formula II, and salts and prodrugs thereof:

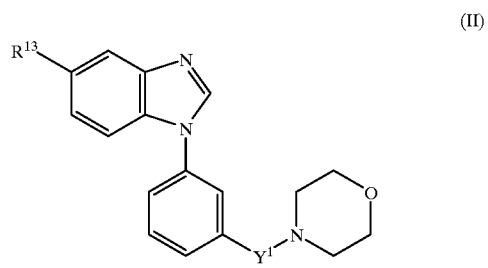

(II)

wherein $Y^1$ represents a methylene (CH$_2$) or carbonyl (C=O) linkage;

$R^{13}$ represents hydrogen, halogen, cyano, nitro, trifluoromethyl, pyrrolyl, furyl, isoxazolyl, amino, $C_{1-6}$ alkylamino, di($C_{1-6}$)akylamino, $C_{1-6}$ alkyl, $C_{1-6}$ alkoxy, $C_{2-6}$ alkylcarbonyl, $C_{1-6}$ alkylsulphonyl or —CR$^4$=NOR$^5$; and $R^4$ and $R^5$ independently represent hydrogen, methyl or ethyl.

Suitably, $Y^1$ represents a carbonyl (C=O) linkage.

Suitably, $R^{13}$ represents $C_{1-6}$ alkyl, especially methyl.

Specific compounds within the scope of the present invention include:

1-[3-(morpholin-4-ylcarbonyl)phenyl]-5-methylbenzimidazole;

1-[3-(N,N-diethylamido)phenyl]-5-methylbenzimidazole;

1-[3-(4-pyridylmethylamido)phenyl]-5-methylbenzimidazole;

1-[3-(2-pyridylmethylamido)phenyl]-5-methylbenzimidazole;

1-[3-(thiomorpholin-4-ylcarbonyl)phenyl]-5-methylbenzimidazole;

1-[3-(4-hydroxypiperidin-1-ylcarbonyl)phenyl]-5-methylbenzimidazole;

1-[3-(morpholin-4-ylmethyl)phenyl]-5-methylbenzimidazole;

1-[3-(imidazol-1-ylmethyl)phenyl]-5-methylbenzimidazole; and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human GABA$_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III:

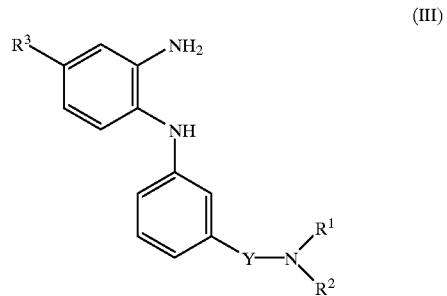

wherein Y, $R^1$, $R^2$ and $R^3$ are as defined above; with formic acid, typically at an elevated temperature.

In another procedure, the compounds according to the present invention in which Y represents a methylene linkage may be prepared by a process which comprises treating a compound of formula IV:

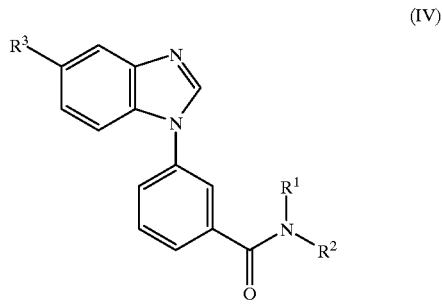

wherein $R^1$, $R^2$ and $R^3$ are as defined above; with a reducing agent such as lithium aluminium hydride.

In a further procedure, the compounds according to the present invention in which Y represents a thiocarbonyl linkage may be prepared by a process which comprises treating the corresponding compound of formula IV as defined above with Lawesson's reagent [2,4-bis(4-methoxyphenyl)-1,3-dithia-2,4-diphosphetane-2,4-disulphide] or phosphorus pentasulphide in a suitable solvent, e.g. pyridine, at ambient or elevated temperatures, suitably at the reflux temperature of the solvent.

In a yet further procedure, the compounds according to the present invention in which Y represents a methylene linkage may be prepared by a process which comprises reacting a compound of formula V with a compound of formula VI:

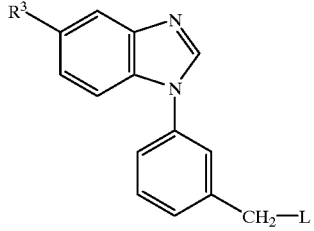

(V)

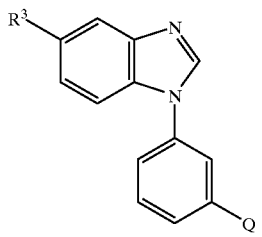

(VI)

wherein $R^1$, $R^2$ and $R^3$ are as defined above, and L represents a suitable leaving group.

The leaving group L is suitably a halogen atom, e.g. chloro, in which case the reaction between compounds V and VI is conveniently carried out by stirring the reactants in a suitable solvent, for example N,N-dimethylformamide, tetrahydrofuran, acetonitrile or dichloromethane, optionally in the presence of a base such as potassium carbonate or triethylamine.

In a still further procedure, the compounds according to the invention in which Y represents a carbonyl linkage, i.e. the compounds of formula IV as defined above, may be prepared by a process which comprises reacting a compound of formula VI as defined above with a compound of formula VII:

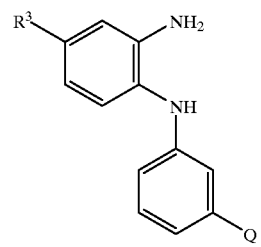

(VII)

wherein $R^3$ is as defined above, and Q represents a reactive carboxylate moiety.

Suitable values for the reactive carboxylate moiety Q include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula VII above wherein Q is an acid chloride moiety may be prepared by treating the corresponding carboxylic acid derivative with thionyl chloride in toluene. Similarly, the intermediates of formula VII wherein Q is an acylimidazole moiety may be prepared by treating the corresponding carboxylic acid derivative with 1,1'-carbonyldiimidazole. Alternatively, the reactive carboxylate moiety Q may be obtained by treating the corresponding compound wherein Q is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula VI.

Typical intermediates of formula V above wherein the leaving group L is a halogen atom may suitably be prepared by treating the appropriate compound of formula VII wherein Q represents carboxy with a reducing agent, for example lithium aluminium hydride, followed by conversion of the primary hydroxy group in the compound thereby obtained into a halogen atom by treatment with a thionyl halide such as thionyl chloride.

The intermediates of formula VII above may suitably be prepared by reacting a compound of formula VIII:

(VIII)

wherein $R^3$ and Q are as defined above; with formic acid, typically at an elevated temperature.

The intermediates of formula III and VIII above may be prepared by methods analogous to those described in EP-A-0616807.

Where they are not commercially available, the starting materials of formula VI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. Indeed, as noted above, the intermediates of formula IV are compounds according to the invention in their own right.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

EXAMPLE 1

1-[3-(Morpholin-4-ylcarbonyl)phenyl]-5-methylbenzimidazole

Step 1: 4-Methyl-3'-carboxy-2-nitrodiphenylamine

4-Methyl-2-nitroaniline, 3-iodobenzoic acid (10 g, 40 mmol), potassium carbonate (5.5 g, 40 mmol) and a catalytic amount of CuI were thoroughly mixed and heated to 230° C. for 4 hours. The reaction mixture was allowed to cool to 100° C. and water added. After cooling to room temperature the solution was rendered acidic by careful addition of glacial acetic acid. The precipitate was filtered off and washed with dichloromethane. Recrystallization from 2-propanol afforded product. Yield 4.3 g.

Step 2: 2-Amino-3'-carboxy-4-methyldiphenylamine

A mixture of 4-methyl-3'-carboxy-2-nitrodiphenylamine (1 g, 3.11 mmol) and palladium on activated carbon (5%, 0.1 g) in MeOH (25 ml) was hydrogenated at ambient pressure until the hydrogen uptake had ceased. The reaction mixture was filtered through celite into a few millilitres of ethereal hydrogen chloride. Evaporation of solvent left the desired product (0.95 g, 2.89 mmol).

Step 3: 1-(3-Carboxyphenyl)-5-methylbenzimidazole

A mixture of 2-amino-3'-carboxy-4-methyldiphenylamine (6.00 g, 14.4 mmol) and formic acid (60 ml) was refluxed for 16 h. After evaporation to dryness, the residue was dissolved in ethyl acetate (100 ml) and washed with water (100 ml). The organic phase was dried and evaporated. The crude product was purified by column chromatography with methylene chloride as the eluent. Yield 4.2 g. $^1$H NMR (250 MHz, DMSO) δ 2.47 (3H, s), 7.21 (1H, dd, J=1.4 Hz), 7.53 (1H, d, J=8.3 Hz), 7.60 (1H, s), 7.75 (1H, t, J=7.8 Hz), 7.95 (1H, m), 8.03 (1H, m), 8.14 (1H, m) and 8.62 (1H, s). MS M$^+$ 253.

Step 4: 1-[3-(Morpholin-4-ylcarbonyl)phenyl]-5-methylbenzimidazole

A mixture of 1-(3-carboxyphenyl)-5-methylbenzimidazole (50 mg, 0.19 mM), 1-(3-dimethylaminopropyl)-3-ethyl carbodiimide, HCl (76 mg, 0.39 mM), hydroxybenzotriazole (53 mg, 0.39 mM) in dimethylformamide (2 ml) was treated with triethylamine (80 μl, 0.39 mM) and morpholine (20 μl, 0.22 mM) and the reaction stirred for 18 hours at room temperature under $N_2$. Dilution with water and extractive work up with ethyl acetate was followed by chromatography on silica gel. Yield 37 mg. $^1$H NMR (360 MHz, DMSO) 2.51 (3H, s), 3.47–3.73 (8H, m), 7.16 (1H, d, J=8.3 Hz), 7.41 (1H, d, J=8.3 Hz), 7.45 and 7.47 (1H, dt, J=1.4 Hz, 7.0 Hz), 7.57–7.60 (3H, m), 7.66 (1H, s) and 8.08 (1H, s). MS M$^+$ 322.

EXAMPLE 2

1-[3-(N,N-Diethylamido)phenyl]-5-methylbenzimidazole

Prepared by an analogous procedure to that described in Example 1 using diethylamine. $^1$H NMR (360 MHz, CDCl$_3$) 1.10–1.24 (6H, m), 2.51 (3H, s), 3.27–3.42 (2H, m), 3.50–3.64 (2H, m), 7.16 (1H, d, J=8.3 Hz), 7.42–7.45 (2H, m), 7.53–7.62 (3H, m), 7.66 (1H, s) and 8.08 (1H, s). MS M$^+$ 308.

EXAMPLE 3

1-[3-(4-Pyridylmethylamido)phenyl]-5-methylbenzimidazole

Prepared by an analogous procedure to that described in Example 1 using 4-pyridylmethylamine. $^1$H NMR (360 MHz, CDCl$_3$) 2.44 (3H, s), 4.68 (2H, d, J=5.9 Hz), 7.09 (1H, d, J=8.3 Hz), 7.25 (1H, d, J=6.0 Hz), 7.35 (1H, d, J=8.3 Hz), 7.49 (1H, s), 7.61–7.66 (2H, m), 7.88 (1H, s), 7.97–8.01 (2H, m), 8.16 (1H, br t) and 8.49 (2H, m). MS M$^+$ 343.

EXAMPLE 4

1-[3-(2-Pyridylmethylamido)phenyl]-5-methylbenzimidazole

Prepared by an analogous procedure to that described in Example 1 using 2-pyridylmethylamine. $^1$H NMR (250 MHz, DMSO) 2.45 (3H, s), 4.61 (2H, d, J=5.9 Hz), 7.19 (1H, d, J=8.7 Hz), 7.26 (1H, dd, J=4.8 and 12.3 Hz), 7.36

(1H, d, J=7.8 Hz), 7.55–7.59 (2H, m), 7.71–7.80 (2H, m), 7.88 (1H, d, J=8.9 Hz), 7.99–8.02 (1H, d, J=7.7 Hz), 8.18 (1H, s), 8.30–8.35 (1H, m), 8.58 (1H, s) and 9.30 (1H, br t, J=5.9 Hz). MS M+ 343.

EXAMPLE 5

1-[3-(Thiomorpholin-4-ylcarbonyl)phenyl]-5-methylbenzimidazole

Prepared by an analogous procedure to that described in Example 1 using thiomorpholine. $^1$H NMR (250 MHz, DMSO) 2.45 (3H, s), 2.67 (4H, br s), 3.63 (2H, br), 3.88 (2H, br), 7.18 (1H, d, J=8.3 Hz), 7.46–7.57 (3H, m), 7.66–7.78 (3H, m) and 8.55 (1H, s). MS M+ 338.

EXAMPLE 6

1-[3-(4-Hydroxypiperidin-1-ylcarbonyl)phenyl]-5-methylbenzimidazole

Prepared by an analogous procedure to that described in Example 1 using 4-hydroxypiperidine. $^1$H NMR (250 MHz, DMSO) 1.39 (2H, br), 1.77 (2H, br), 2.45 (3H, s), 3.24 (1H, br), 3.52 (2H, br), 3.72 (2H, br), 4.82 (1H, d, J=3.9 Hz), 7.17 (1H, d, J=8.3 Hz), 7.45–7.57 (3H, m), 7.65–7.74 (3H, m) and 8.54 (1H, s). MS M+ 336.

EXAMPLE 7

1-[3-(Morpholin-4-ylmethyl)phenyl]-5-methylbenzimidazole

Step 1: 1-(3-Hydroxymethylphenyl)-5-methylbenzimidazole 1-(3-Carboxyphenyl)-5-methylbenzimidazole (2 g, 0.079 mM) was dissolved in dry tetrahydrofuran (100 ml) and cooled to 0° C. Lithium aluminium hydride (7.9 ml, 1.0 M solution) was added dropwise over 10 minutes. After complete addition the reaction was heated to reflux for 4 hours. The reaction was cooled and quenched by addition of water (2 ml) and 2N sodium hydroxide (4 ml). The reaction was diluted with ethyl acetate and filtered through hyflo, washing with ethyl acetate. Dried over magnesium sulphate and evaporated (1.2 g). MS M+ 239.

Step 2: 1-(3-Chloromethylphenyl)-5-methylbenzimidazole HCl 1-(3-Hydroxymethylphenyl)-5-methylbenzimidazole (0.3 g, 1.26 mM) was dissolved in dichloromethane (3 ml). Thionyl chloride (92 μl, 1.26 mM) was added and the reaction stirred for 30 minutes. Solvent evaporated to obtain product (0.36 g). MS M+ 957.

Step 3: 1-[3-(Morpholin-4-ylmethyl)phenyl]-5-methylbenzimidazole 1-(3-Chloromethyl)phenyl-5-methylbenzimidazole (0.11 g, 0.37 mM) was dissolved in dimethylformamide (5 ml). Potassium carbonate (52 mg, 0.37 mM) was added followed by morpholine (97 μl, 1.11 mM) and the reaction heated to 80° C. for 18 hours. Dilution with water and extraction with ethyl acetate was followed by chromatography over silica gel (61 mg). $^1$H NMR (360 MHz, DMSO, TFA) 2.54 (3H, s), 3.17 (2H, br), 3.31 (2H, br), 3.18 (2H, br), 3.95 (2H, br), 4.50 (2H, s), 7.49 (1H, d, J=5.7 Hz). 7.78–7.94 (5H, m), 8.08 (1H, s) and 9.94 (1H, s). MS M+ 308.

EXAMPLE 8

1-[3-(Imidazol-1-ylmethyl)phenyl]5-methylbenzimidazole 1-(3-Chloromethylphenyl)-5-methylbenzimidazole (0.1 g, 0.34 mM) was dissolved in dichloromethane (5 ml), imidazole (92 mg, 1.36 mM) was added and the reaction heated to reflux for 18 hours, then diluted with water and extracted into ethyl acetate, dried (MgSO$_4$) and purified by silica chromatography. Yield 34 mg. $^1$H NMR (250 Mz, DMSO) δ 2.44 (3H, s), 5.32 (2H, s), 6.92 (1H, t, J=0.9 Hz), 7.16 (1H, d, J=8.3 Hz), 7.29–7.35 (2H, m), 7.47 (1H, d, J=8.3 Hz), 7.57–7.61 (4H, m), 7.83 (1H, t, J=0.9 Hz) and 8.49 (1H, s). MS m/e 289.

What is claimed is:

1. A compound represented by formula II, and salts thereof:

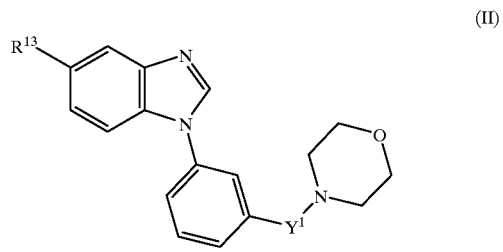

(II)

wherein

Y$^1$ represents a methylene (CH$_2$) or carbonyl (C=O) linkage;

R$^{13}$ represents a hydrogen, halogen, cyano, nitro, trifluoromethyl, pyrrolyl, furyl, isoxazolyl, amino, C$_{1-6}$alkylamino, C$_{1-6}$alkyl, C$_{1-6}$alkoxy, C$_{2-6}$alkylcarbonyl, C$_{1-6}$alkylsulphonyl or —CR$^4$=NOR$^5$; and R$^4$ and R$^5$ independently represent hydrogen, methyl or ethyl.

2. A compound as claimed in claim 1 wherein Y$^1$ represents a carbonyl (C=O) linkage.

3. A compound as claimed in claim 1 wherein R$^{13}$ represents C$_{1-6}$ alkyl.

4. A compound selected from:

1-[3-(morpholin-4-ylcarbonyl)phenyl]-5-methylbenzimidazole;

1-[3-(morpholin-4-ylmethyl)phenyl]-5-methylbenzimidazole;

and salts thereof.

5. A pharmaceutical composition comprising a compound of formula II as defined in claim 1 or a pharmaceutically acceptable salt thereof in association with a pharmaceutically acceptable carrier.

6. A method for the treatment of anxiety which comprises administering to a patient in need of such treatment an effective amount of a compound of formula II as defined in claim 1 or a pharmaceutically acceptable salt thereof.

7. A method for the treatment of convulsions which comprises administering to a patient in need of such treatment an effective amount of a compound of formula II as defined in claim 1 or a pharmaceutically acceptable salt thereof.

* * * * *